US011020574B2

(12) United States Patent
Rajkovic

(10) Patent No.: US 11,020,574 B2
(45) Date of Patent: Jun. 1, 2021

(54) DISPOSABLE GYNECOLOGIC INSTRUMENT FOR DILATION OF BODY CAVITIES BY FLUID INJECTION

(71) Applicant: INOVE DOO BEOGRAD, Serbia (RS)

(72) Inventor: Dobrivoje Rajkovic, Belgrade (RS)

(73) Assignee: INOVE DOO BEOGRAD, Belgrade (RS)

( * ) Notice: Subject to any disclaimer, the term of this patent is extended or adjusted under 35 U.S.C. 154(b) by 120 days.

(21) Appl. No.: 16/126,926

(22) Filed: Sep. 10, 2018

(65) Prior Publication Data

US 2019/0240466 A1 Aug. 8, 2019

Related U.S. Application Data

(63) Continuation of application No. 12/990,466, filed as application No. PCT/RS2009/000013 on Mar. 31, 2009, now abandoned.

(30) Foreign Application Priority Data

Mar. 31, 2008 (RS) .................................. P2008-0130

(51) Int. Cl.
*A61M 29/02* (2006.01)
(52) U.S. Cl.
CPC .................................. *A61M 29/02* (2013.01)
(58) Field of Classification Search
CPC ...... A61M 29/02; A61M 3/02; A61M 3/0233; A61M 1/0058; A61B 17/3203; A61B 18/1442; A61B 18/1482
See application file for complete search history.

(56) References Cited

U.S. PATENT DOCUMENTS 4,611,602 A * 9/1986 Bolduc ............. A61M 25/1018
600/560
5,350,356 A * 9/1994 Bales .................. A61M 3/0233
604/27

(Continued)

FOREIGN PATENT DOCUMENTS

WO WO-0202175 A1 * 1/2002 ............ A61M 29/02

*Primary Examiner* — Phong Son H Dang
(74) *Attorney, Agent, or Firm* — Ladas & Parry LLP

(57) ABSTRACT

Disposable gynecologic instrument for dilation of body cavities by fluid injection, the construction according to the invention, include the instrument body (1) to which it has from the bottom tightly fixed a handle (2) with the reservoir (3) whilst is on the frontal part of the instrument body (1) projected is the trigger (4) positioned slidingly and designed for pressing with two fingers, which is by screw (41) connected to the main piston (42) movable within the cylinder, around which is placed a bigger spring (43) and where the outlet of cylinder is connected to one branch of the three-way pipeline (44), the other two of which are connected, one on the upper irreversible valve (12), and the other to the lower irreversible valve (22); and where is also on the front side of the instrument body (1) by screw thread and sealingly attached the main pipe (5), formed with longitudinal ribs (51) positioned crosswise and a series of aslope placed ribs (52) of circular perimeter, which increase the stiffness of the main pipe (5) in which projected part is by screw thread fixed the support (6) for the body (100) of the dilation probe with the holding fixture (7) of the dilation balloon, and where on the body (1), on the upper right side is the button (8) of a squeezer with vent protector (9), while in front of it is the holder (10) for the small spring (11) of the upper irreversible valve (12).

8 Claims, 3 Drawing Sheets

(56) References Cited

U.S. PATENT DOCUMENTS

| | | | | |
|---|---|---|---|---|
| 5,690,669 A | * | 11/1997 | Sauer | A61M 16/0472 606/192 |
| 6,109,264 A | * | 8/2000 | Sauer | A61M 16/0472 128/200.26 |
| 2002/0004942 A1 | * | 1/2002 | Bryan | A23G 9/44 800/288 |
| 2004/0230157 A1 | * | 11/2004 | Perry | A61M 5/14566 604/99.02 |

* cited by examiner

DISPOSABLE GYNECOLOGIC INSTRUMENT FOR DILATION OF BODY CAVITIES BY FLUID INJECTION

CROSS REFERENCE TO RELATED APPLICATIONS

This application is a continuation of U.S. application Ser. No. 12/990,466 filed 29 Oct. 2020, which is a '371 of PCT/RS09/00013 31 Mar. 2009 which claims priority of P2008-0130 RS filed 31 Mar. 2008.

TECHNICAL FIELD

Disposable gynecologic instrument for dilation of body cavities by fluid injection, according to this invention, belongs to the field of medicine, to the medicinal apparatus, devices, or instruments for performing medical examination of interior of body cavities or tubular organs, particularly to the gynecologic or obstetrics instruments for opening or increasing of visual field in interior of body cavities or to the devices working on syringe principle, where incompressible fluid inside of a syringe reservoir is pressed by piston, i.e belongs to the devices for dilation of body cavities—dilators realized with inflatable materials.
(Int.Cl$^8$.: A 61B 1/32 (2008.01); A 61M 5/315 (2008.01); A 61M 29/04 (2008.01)

TECHNICAL PROBLEM

Disposable gynecologic instrument for dilation of body cavities by fluid injection, according to the invention, resolve the problem of construction of such medical instrument which by its simple, practical and safe structure resolve the problem of gradual (controlled) dilation of body cavities so that prevent the damage of collagen and muscle tissues, which surround the body cavities, particularly woman cervix, which instrument may be realized as a whole with a dilation probe, containing cannula for providing stiffness, and through which and/or around which will pass the incompressible fluid which will expand the dilation probe (catheter balloon) made of particularly woven material, which will allow spreading till an previously determined diameter, so that it obtains an cylindrical shape.

Disposable gynecologic instrument for dilation of body cavities by fluid injection, according to the invention, solves the problem of simple construction of an disposable gynecologic instrument, simply for use, which because of its suitable handle solve the problem of gradual (controlled) dilation of body cavities realized by simple pressure of two fingers, whereas the instruments are delivered to the user packed, sterilized and ready for use, and which after use may be either completely rejected or returned back to the manufacturer as secondary raw material where, at the manufacturer, reservoir may be re-filled, replaced used dilation probe (catheter balloon), where folding the instrument may be finished, done its sterilization, packaging and return to the market.

BACKGROUND ART

It is known that in the practice are used various methods of expansion (dilation) of body cavities, in which it is necessary to be overcomed the natural resistance of muscle tissue, especially at the uterine cervix in women. As proved in practice, openings, after the spread of these, retain their increased diameter for a few hours, and in the beginning of the last century it was developed the application of cylindrical shaped metal inserts with diameters from 4 mm to 12 mm, which are inserted starting from narrowest, and than wider and next wider serialy inserted and extracted after some time when the cavity is adjusted to a certain diameter. This, so-called, Hegar's method, which is now widely applied, has a series of shortcomings whereas the biggest problem was damage of muscle fibers, and also a high probability in occurrence of various infections in the application of this method. The basic drawback is the application of large forces during insertion of these inserts one by one, as well occurrence of friction during insertion of inserts, which is also followed by pain during this procedure.

In recent years, by the development of technology come in sight a large number of different solutions based on use of various dilation probes which makes the dilation of body cavities applying radial forces created by a radial expanding of dilation probe after insertion in the body cavity the probe with the narrowest diameter.

Like in the professional literature, so in patent documentation, there may be found a whole range of different solutions which are based on the application of dilation probe that is by suitable medical instrument inserted in the body cavity, and then, applying the hydraulic pressure gradually radially spreading the part of probe inserted in the body opening as to a previously determined diameter.

Considering the problems and disadvantages of known solutions, eg. making the replacement of materials that are unsuitable or even unallowed to contact with human tissue, or disadvantages in serial manufacturing of dilation probes in certain features, or design of various medical instruments capable to achieve the appropriate radial pressure that would allow a gradual and evenly spread of body cavity to a certain size, there has been reached a construction of disposable gynecologic instrument for dilation of body cavities by fluid injection, according to this invention.

DISCLOSURE OF THE INVENTION

Disposable gynecologic instrument for dilation of body cavities by fluid injection, according to the invention, represent a manual hydraulic pump, which in appearance resembles a gun, and is presented as a whole with dilation probe (shown on a particular drawing), and which is located and locked on the top of the cannula). This gynecological instrument consists of a instrument body with an reservoir for incompressible fluid in the handle, whereas the instrument body and a handle are made in whole form and are presented as so-called pistol handle. Next on the body of the instrument is the trigger the pressing of which (by controlled force) starts the piston pressing the fluid volume within the cylinder filled with incompressible fluid, and so pumps out the incompressible fluid from the reservoir through the lower cannula and irreversible valve (to prevent the return of incompressible fluid back in the reservoir) and pushes fluid through the second irreversible valve (to prevent return of incompressible fluid from catheter balloon of dilation probe), into the main pipe, and then into catheter balloon of dilation probe, which is radially spreaded, causing by this way a gradually spreading of the body cavity into which is inserted the balloon of dilation probe. The main instruments pipe is by screw thread attached to the front of the instrument body, and on the protruding end of the main pipe is by screw thread fixed support of a catheter balloon of the dilation probe, which is by the lock of catheter balloon fixed to the support. On the body of the gynecologic instrument is anticipated a vent structure, which after the use of the gynecologic instrument and realization of the anticipated physical enlargement of the opening (when the catheter balloon is fully inflated) allows to reduce the pressure in it, by simply removal the vent lock, which allows return of incompressible fluid into the reservoir, and lowering the piston to the end of piston stroke, vent lock will lock the piston in his final position, which disabled his return to the operating position, and thus at the same time prevents the repeated use of gynecology instrument.

BRIEF DESCRIPTION OF DRAWINGS

Disposable gynecologic instrument for dilation of body cavities by fluid injection, according to the invention, is shown on the attached drawings in which.

DETAILED DESCRIPTION OF THE INVENTION

Figure 1:
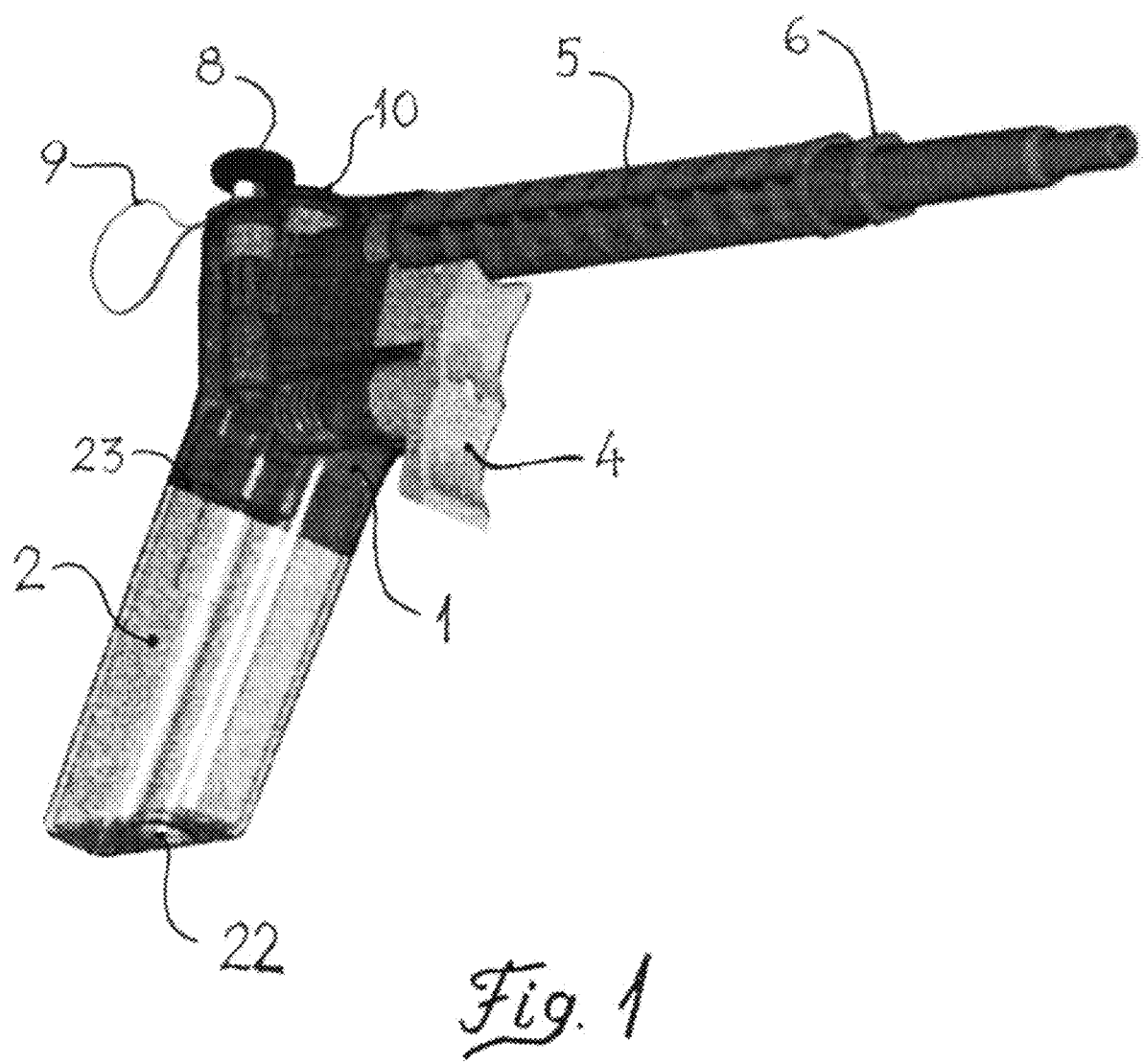
FIG. 1 shows the general layout of disposable gynecologic instrument for dilation of body cavities by fluid injection.

In FIG. 1 is shown disposable gynecologic instrument for dilation of body cavities by fluid injection, according to the invention, which represent a manual hydraulic pump, which consists of the instrument body 1 to which is from the bottom tightly fixed a handle 2 with the reservoir 3. At the frontal part of the instrument body 1, projected is the trigger 4 which is adapted for pressing with two fingers, in order to be easier, and by the controlled force, achieved a higher pressure in the system. On the front of the instrument body 1 is by screw thread attached a main pipe 5, in the projected part of which is by screw thread fastened a support 6 for the body of dilation probe with the holding fixture 7 of the dilation balloon (where the dilation probe is not shown, for example, realized as a hollow cannula of polypropylene, which is wrapped by internal elastic rubber layer, which is all over wrapped by a weaved layer of polyethylene material that may be evenly spreaded by its diameter—to previously determined diameter value—regardless of the pressure which causes this spreading, and where is all over wrapped an outer rubber layer). On the body 1 on the upper right side is the button 8 of a squeezer with vent protector 9, and in front of it is the holder 10 for the small spring 11 of the upper irreversible valve 12.

Figure 2:
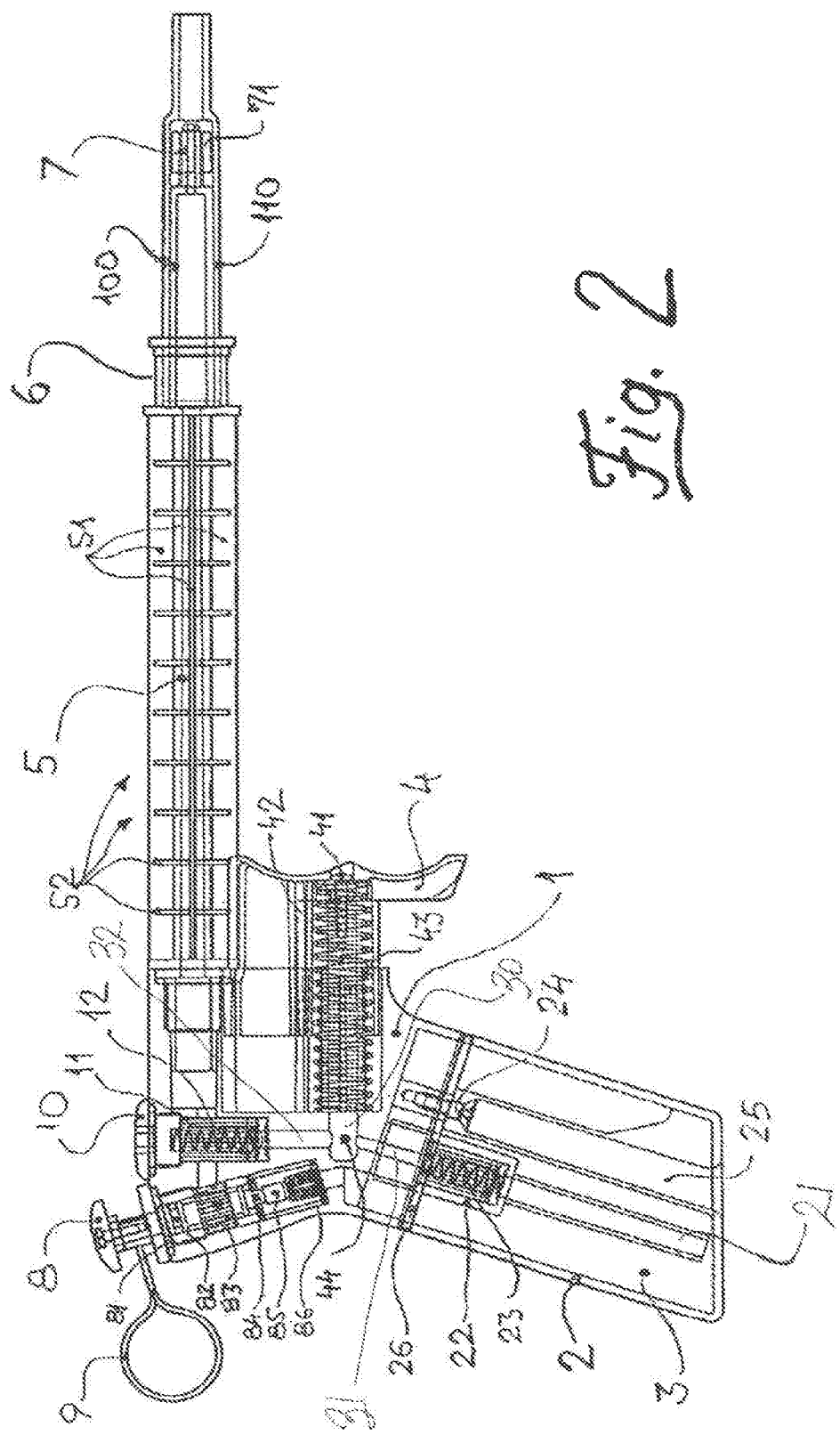
FIG. 2 shows a lateral view to the structure of disposable gynecologic instrument for dilation of body cavities by fluid injection, according to the invention.

FIG. 2 shows a lateral view to the structure of disposable gynecologic instrument for dilation of body cavities by fluid injection, according to the invention, whereas may be seen its detailed structure, which consists of the instrument body 1 to which is from the bottom tightly fixed a handle 2 with the reservoir 3 which is positioned inside the handle 2. Within the reservoir 3 extended is the lower cannula 21 through which the incompressible fluid passes from the reservoir into the body 1, which cannula 21 to its upper has a irreversible-valve 22, in which, in the seat of the sealing ball, positioned sealing ball is pushed downwards by a small spring 23 closing, such a way, the irreversible-valve 22 so that it does not allow the return of incompressible fluid into the reservoir 3. Handle 2 is fixed to the body 1 underneath by the screw 24 within the cavity 25, and by all the upper edge of the handle 2 where is settled the reservoir gasket 26. Body 1 with the handle 2 form as a whole so-called pistol handle, while in the upper part of the front side of the instrument body 1 is by screw thread and sealingly attached the main pipe 5, formed with longitudinal ribs 51 positioned crosswise in order to strengthen the main pipe 5 with a series of aslope placed ribs 52 of circular perimeter, which increase the stiffness of the main pipe 5. At the extended end of the main pipe 5 by screwed thread fastened is support 6 for the body 100 of the dilation probe closed with a closure 110 through which is dragged a top 120 of the dilation probe that is implanted into body cavity and the holding fixture 7 hollow cannula, mandrel 160 with dilation balloon of the probe (which is not shown). At the bottom part of the front side on the body 1, protruded, slidingly is set trigger 4, which pump incompressible fluid into the main pipe 5. Trigger 4 is designed for pressing with two fingers in order to enable easier control of the pressure force, and to achieve a higher pressure in the system, and thus make a gradual increase of balloon in the dilation probe. Trigger 4 is a by screw 41 connected to the main piston 42, which is suppressing a great resistance of the bigger spring 43 positioned around the cylinder in which the main piston 42 is connected to one branch 30 of the three-way pipeline 44, while the other two branches 31, 32 through irreversible valves are connected so, that one to the upper irreversible valve 12, which provides that the incompressible fluid can not return from the main pipe 5, ie. from catheter balloon of the dilation probe, and other to the lower irreversible valve 22 to prevent the return of the incompressible fluid into reservoir 3. Upper irreversible valve 12 on its upper end has a holder 10 for the small spring 11 of the upper irreversible valve 12. Vent arrangement is located on the upper rear end and consists of button 8 of a squeezer with vent protector 9, while is along the axis below the O-ring 81 placed stopper 82 of exhaust valve, piston 83 of the vent movable within the vent piston cylinder, below which is located the special gasket 84 under which is lock 85 of the vent piston, whilst at the bottom is positioned a special gasket 86.

Figure 3:
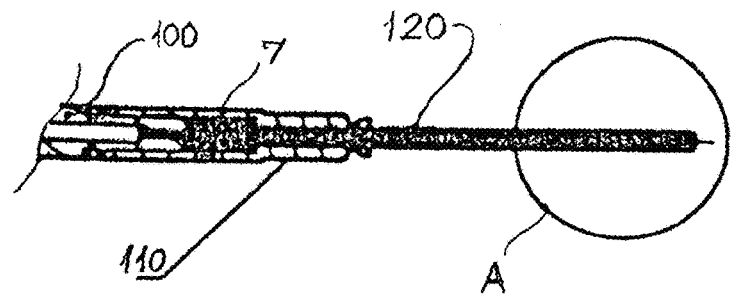
FIG. 3 shows the general layout to the section of dilation probe with the body closed with a closure through which is dragged a top of dilation probe that is implantable into the body cavity.

FIG. 3 shows the general layout of the section of dilation probes body 100 closed with a closure 110 through which is dragged a top 120 of the dilation probe that is implanted into the body cavity. On holding fixture 7 of the hollow cannula, of mandrel 160 is locked a catheter balloon of the dilation probe by lock 71 so that the is achived the stiffness of the arrangement which facilitates the entry into the body cavity to be spread.

Figure 4:
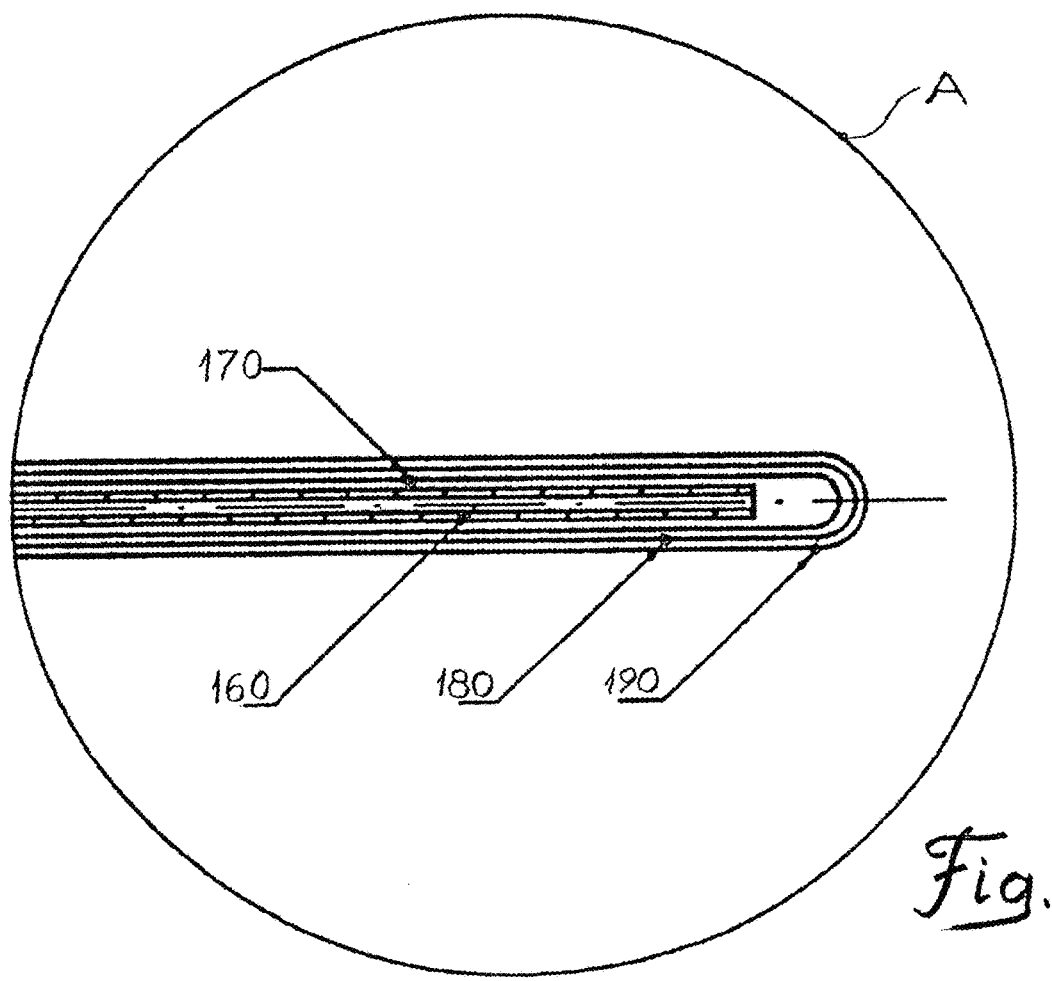
FIG. 4 shows an enlarged detail A from FIG. 3, which shows the structure of the top of dilation probe presented with the arrangement of layers, which probe is implemented into the body cavity, and which layers then are spreaded under action of incompressible fluid pushed by piston, broadening gradually, by this way, the sides of the body cavity.

FIG. 4, which is an enlarged detail A from FIG. 3, shows the detailed construction of layers of probe 120, which is implemented in the body cavity, and whose layers, by actions of liquid supressed by main piston 42, become wider, gradually broadening to the way the walls of the body cavity. It may be seen that is around the hollow cannula of the mandrel 160 wrapped an inner-rubber layer 170, which all over itself has a strengthened layer made of woven polyethylene material 180 that may evenly spread by the extent to an in advance determined values in diameter, regardless of the applied pressure from the inside, which this increase in diameter will not be affected by the shortening by length, and will allow later that this dilation balloon may be returned to its initial diameter without banding and ruffle of material. All over is enwrapped the outer rubber layer 190, where should be emphasized, that in advance determined values of the diameter of the balloon depends of its application, ie. that the dilation balloon is made for standard use, for primipara, for the women who bear several times, etc.

BEST MODE FOR CARRYING OUT OF THE INVENTION

Disposable gynecologic instrument for dilation of body cavities by fluid injection, according to the invention, is filled with incompressible fluid (usually distilled water or the like.) through the hole on the back of the upper part of the body 1, and preferably has to be filled so that the main pipe 5, as well as catheter balloon of the dilation probe are thoroughly fulfilled, and then during the execution of assembly, the opening is closed by inserting special gasket 86 and above it, all other parts of vent structure and when the vent protector 9 is inserted and made sterilization and packaging, disposable gynecologic instrument for dilation of body cavities by fluid injection is fully ready for use.

Its function is executed by pressing the trigger 4 when the incompressible fluid is with main piston 42 pumped out from the reservoir 3 into the main pipe 5 and further into dilation probe, ie. into the catheter balloon. As already said, the irreversible valves, 22 at the inlet of the cylinder, preventing the return of incompessible fluid in the reservoir 3, and valve 12 at the outlet from the cylinder prevent the return of incompessible fluid from the balloon.

When the probe balloon is inflated to the desired diameter size of the body cavity, ie. when it is sufficiently broad, it is necessary to reduce the pressure in the balloon. This would be done, first by removal of the vent protector 9 by simply pulling the ring, which will release the shaft of the vent piston 83, and later by pressing the button 8 vent piston 83 moves within the cylinder until it came down to the end, when lock 85 of the vent piston lock it in the bottom position, preventing his return to the original position and disable Disposable gynecologic instrument for dilation of body cavities by fluid injection disposable gynecologic instrument for dilation of body cavities by fluid injection for re-use.

Disposable gynecologic instrument for dilation of body cavities by fluid injection, according to the invention, is now possible or to be rejected, or to be returned to the manufacturer as a secondary raw material, where at the manufacturers the reservoir may be re-filled, replaced the used dilation probe (catheter balloon), finished the folding of the instrument, the sterilization, packaging and return to the market.

Although is the disposable gynecologic instrument for dilation of body cavities by fluid injection described with reference to a specific embodiment shown in the drawings, it is clear that the details of construction and individual achievements, as well as certain phases of the production process may be modified in relation to the one described and shown on the drawings, this will not depart from the concept of subject invention as defined in the following claims.

The invention claimed is:
1. A disposable gynecologic instrument for injection of fluid into a dilation probe, the instrument comprising an instrument body that comprises:
  (a) a fluid inlet for introducing the fluid into the instrument body;
  (b) a handle at a bottom portion of the instrument body for gripping the instrument body, the handle comprising a reservoir in the bottom portion of the instrument body for holding the fluid;
  (c) a main pipe at an upper portion of the instrument body for guiding fluid from the instrument body into the dilation probe;
  (d) a trigger in a center portion of the instrument body comprising a piston slidable within a cylinder from a first position to a second position; and
  (e) fluid communication means for providing fluid connection between the fluid inlet, the reservoir, the cylinder and the main pipe so that the fluid introduced into the instrument body through the fluid inlet can flow to the reservoir, cylinder and main pipe, the fluid communication means comprising a three-way pipeline having three branches which meet at a three-way junction, including a first branch extending from the reservoir to the junction, a second branch extending from the cylinder to the junction, and a third branch extending from the main pipe to the junction,
wherein the first branch comprises a lower irreversible valve below the junction for preventing the fluid from the junction from returning to the reservoir and the third branch comprises an upper irreversible valve above the junction for preventing the fluid from the main pipe from returning to the junction, and
wherein the piston is configured and arranged within the instrument body so that, when the instrument body is filled with the fluid and the trigger is pressed to slide the piston through the cylinder from the first position to the second position, sliding of the piston presses the fluid in the second branch toward the junction and forces fluid from the reservoir to and through the junction and to and through the main pipe for injection into the dilation probe.

2. The disposable gynecologic instrument according to claim 1, wherein the trigger is sized so that it can be pressed with two fingers.

3. The disposable gynecologic instrument according to claim 1, comprising a spring within the cylinder and around the piston.

4. The disposable gynecologic instrument according to claim 1, wherein the main pipe is formed with longitudinal ribs disposed crosswise and a series of spaced ribs of circular perimeter that are inclined with respect to the longitudinal ribs.

5. An apparatus comprising the disposable gynecologic instrument according to claim 1, an inflatable dilation probe and means for attaching the dilation probe to an end of the main pipe that projects from the instrument body.

6. The apparatus according to claim 5, wherein the disposable gynecologic instrument comprises a vent arrangement on an upper rear end of the instrument body for reducing pressure in the dilation probe when the dilation probe is inflated, the vent arrangement comprising a vent piston that is releasable from a first position wherein the vent piston prevents release of pressure from the inflated dilation balloon to a second position wherein the vent piston allows release of pressure from the inflated dilation probe, wherein a vent protector is detachably mounted on the instrument body and prevents the vent piston from releasing from the first position to the second position unless and until the vent protector is detached from the instrument body.

7. The apparatus according to claim 5, wherein the dilation probe comprises a hollow mandrel, an inner layer of rubber wrapped around the mandrel, a layer of woven material on the inner layer of rubber and an outer layer of rubber on the layer of woven material.

8. The apparatus according to claim 7, wherein the woven material comprises polyethylene.

* * * * *